United States Patent
Osypka et al.

(10) Patent No.: US 12,290,646 B2
(45) Date of Patent: May 6, 2025

(54) DEFLECTION INDICATOR FOR DEFLECTABLE VASCULAR CATHETER

(71) Applicant: Oscor Inc., Palm Harbor, FL (US)

(72) Inventors: Thomas P. Osypka, Palm Harbor, FL (US); Andrew J. Enerson, New Port Richey, FL (US); Michael John Gelineau, Lutz, FL (US); Chet Michael, Tampa, FL (US)

(73) Assignee: Oscor Inc., Palm Harbor, FL (US)

( * ) Notice: Subject to any disclaimer, the term of this patent is extended or adjusted under 35 U.S.C. 154(b) by 910 days.

(21) Appl. No.: 17/376,798

(22) Filed: Jul. 15, 2021

(65) Prior Publication Data

US 2021/0386971 A1    Dec. 16, 2021

Related U.S. Application Data

(63) Continuation-in-part of application No. 29/737,784, filed on Jun. 11, 2020, now Pat. No. Des. 940,307, and a continuation-in-part of application No. 29/737,782, filed on Jun. 11, 2020, now Pat. No. Des. 940,306.

(60) Provisional application No. 63/052,200, filed on Jul. 15, 2020.

(51) Int. Cl.
*A61M 25/01* (2006.01)
*A61B 18/14* (2006.01)
*A61B 17/34* (2006.01)
*A61B 18/00* (2006.01)

(52) U.S. Cl.
CPC ..... *A61M 25/0136* (2013.01); *A61B 18/1492* (2013.01); *A61B 17/3421* (2013.01); *A61B 2018/00345* (2013.01); *A61B 2018/00577* (2013.01); *A61M 2205/583* (2013.01)

(58) Field of Classification Search
CPC .......... A61M 25/0136; A61B 17/3421; A61B 18/1492; A61B 2018/00345; A61B 2018/00577; A61B 2205/583
See application file for complete search history.

(56) References Cited

U.S. PATENT DOCUMENTS

| | | | |
|---|---|---|---|
| 9,498,602 B2 | 11/2016 | Osypka et al. | |
| 9,572,957 B2 | 2/2017 | Osypka et al. | |
| 9,907,570 B2 | 3/2018 | Osypka et al. | |
| 9,913,684 B2 | 3/2018 | Osypka | |
| 2018/0214669 A1* | 8/2018 | Davies | A61M 25/0147 |
| 2020/0061340 A1* | 2/2020 | Mixter | A61B 8/4466 |

\* cited by examiner

*Primary Examiner* — Eun Hwa Kim
*Assistant Examiner* — Catherine Premraj
(74) *Attorney, Agent, or Firm* — Michael F. Scalise

(57) ABSTRACT

A deflectable catheter is disclosed that includes a proximal handle, an elongated catheter shaft extending distally from the proximal handle and including a deflectable distal end portion, a drive mechanism associated with the proximal handle for deflecting the distal end portion of the catheter shaft between a first position where the distal end portion of the catheter shaft is aligned with an axis of the catheter shaft and a second position where the distal end portion of the catheter shaft is deflected angularly away from the axis of the catheter shaft, and indicator means associated with the drive mechanism for providing a visual indication of the position of the drive mechanism, which corresponds to a degree of curved deflection of the deflectable distal end portion of the catheter shaft.

20 Claims, 6 Drawing Sheets

DEFLECTION INDICATOR FOR DEFLECTABLE VASCULAR CATHETER

CROSS-REFERENCE TO RELATED APPLICATION

The subject application claims the benefit of priority to U.S. Provisional Patent Application Ser. No. 63/052,200, which was filed on Jul. 15, 2020, U.S. Design patent application Ser. No. 29/737,784, which was filed on Jun. 11, 2020, and U.S. Design patent application Ser. No. 29/737,782, which was filed on Jun. 11, 2020, the contents of which are incorporated by reference herein in their entireties.

BACKGROUND OF THE INVENTION

1. Field of the Invention

The subject invention is directed to surgical instrumentation, and more particularly, to a feature for indicating a degree or amount of deflection associated with a distal end portion of a deflectable vascular catheter.

2. Description of Related Art

Steerable catheters or guiding sheaths are well known in the art. They are used for vascular access and the delivery of therapeutic devices such as stents, anchors and drugs to targeted areas in the vascular system of the human body. They can also be used as vascular ablation catheters, for example in renal ablation procedures.

Deflectable sheaths can be uni-directional or bi-directional, and they are typically available in sheath dimeter sizes ranging from 4 F to 20 F. These devices can be designed with deflection angles that vary from 90 degrees to 270 degrees, and they can be designed with various tip formations, shaft stiffness and handle configurations.

Examples of steerable catheters or guiding sheaths with deflectable distal end portions that are configured for use in conjunction with the subject invention are disclosed in commonly assigned U.S. Pat. Nos. 9,498,602; 9,572,957; 9,907,570; and 9,913,684, the disclosures of which are herein incorporated by reference in their entireties.

The deflection curve of the distal end of the catheter sheath allows a surgeon to access complex vasculature in a very short period of time, as compared to the use of a non-deflectable sheath that has a fixed distal curvature. Typically, deflectable sheaths feature a deflection curve whereby the distal tip deflects in a single plane. When the catheter sheath is deployed within the vascular system of a patient, the amount of deflection is usually determined through visual observation under X-ray of a radiopaque marker band located on the distal-most tip of the catheter.

It would be beneficial to provide an alternative means for a surgeon to determine the amount or degree of deflection of the distal end portion of a steerable vascular catheter within the vasculature of a patient, without the use of X-ray observation techniques.

SUMMARY OF THE INVENTION

The subject invention is directed to a new and useful deflectable vascular catheter that includes a proximal handle assembly, an elongated catheter shaft extending distally from the proximal handle assembly and including a deflectable distal end portion, and a drive mechanism that is operatively associated with an interior cavity of the proximal handle assembly for effectuating angular deflection of the distal end portion of the catheter shaft.

More particularly, the drive mechanism is adapted and configured to steer or otherwise move the distal end portion of the catheter shaft between a first position where the distal end portion of the catheter shaft is axially aligned with a longitudinal axis of the catheter shaft and a second position where the distal end portion of the catheter shaft is deflected angularly away from the longitudinal axis of the catheter shaft. It is envisioned that the distal end portion of the catheter shaft could be configured with a maximum curved deflection angle that ranges from 90 degrees to 270 degrees.

In accordance with a preferred embodiment of the subject invention, the catheter also includes indicator means associated with the drive mechanism for providing a visual indication of the position of the drive mechanism, which corresponds to an amount or degree of curved or angular deflection of the deflectable distal end portion of the catheter shaft. Thus, a surgeon can readily determine the amount or degree of curved deflection without the use of X-ray observation techniques.

Preferably, the drive mechanism includes a linear drive screw that is mounted for reciprocal axial movement within the interior cavity of the proximal handle assembly, and the indicator means includes indicia such as numbers or symbols, contrasting colored features, or observable structural features provided on or associated with at least a portion of the linear drive screw. In addition, a window or portal is formed in the proximal handle assembly at a location that is aligned with the linear drive screw for viewing at least the portion of the linear drive screw that includes the indicator means as the linear drive screw moves within the interior cavity of the proximal handle assembly to steer the distal end portion of the catheter shaft.

The deflectable vascular catheter of the subject invention further includes a rotatable control knob that is operatively associated with a distal end portion of the proximal handle assembly for moving the linear drive screw. The window is located adjacent or proximal to the rotatable control knob. It is envisioned that the catheter shaft could be configured as a guiding sheath, an ablation catheter, an irrigation catheter, a drainage catheter or the like.

The subject invention is also directed to a deflectable vascular catheter that includes a proximal handle assembly, an elongated catheter shaft extending distally from the proximal handle assembly and including a deflectable distal end portion, a linear drive screw mounted for axial movement within an interior cavity of the proximal handle assembly for effectuating angular deflection of the distal end portion of the catheter shaft, and a window formed in the proximal handle assembly at a location that is aligned with the linear drive screw for viewing at least a portion of the linear drive screw as the linear drive screw moves within the interior cavity of the proximal handle assembly to steer the distal end portion of the catheter shaft, wherein at least the portion of the linear drive screw that is aligned with the window is of a color that is in contrast to a color of the proximal handle assembly that surrounds the window, to provide a visual indication to an observer of the amount or degree of deflection of the distal end portion of the catheter shaft.

The subject invention is also directed to a deflectable vascular catheter that includes a proximal handle assembly defining a longitudinal axis, an elongated catheter shaft extending distally from the proximal handle assembly and including a deflectable distal end portion, a linear drive screw mounted for axial movement within an interior cavity of the proximal handle assembly for effectuating angular deflection of the distal end portion of the catheter shaft, a deflection indicator operatively associated with the linear drive screw and configured to move in tandem therewith, and a window formed in the proximal handle assembly at a location that is aligned with the linear drive screw for viewing movement of the deflection indicator. The catheter shaft is preferably configured as a guiding sheath, and the guiding sheath preferably has a diameter of ⅘ F or 12 F. Here, the proximal handle assembly is preferably no longer than 5 cm in axial length, which unique in the art.

These and other features of deflectable vascular catheter of the subject invention will become more readily apparent to those having ordinary skill in the art to which the subject invention appertains from the following description of the drawings.

BRIEF DESCRIPTION OF THE DRAWINGS

So that those skilled in the art will readily understand how to make and use the deflectable vascular catheter of the subject invention without undue experimentation, reference may be made to the figures wherein.

DETAILED DESCRIPTION OF THE PREFERRED EMBODIMENTS

Figure 1:
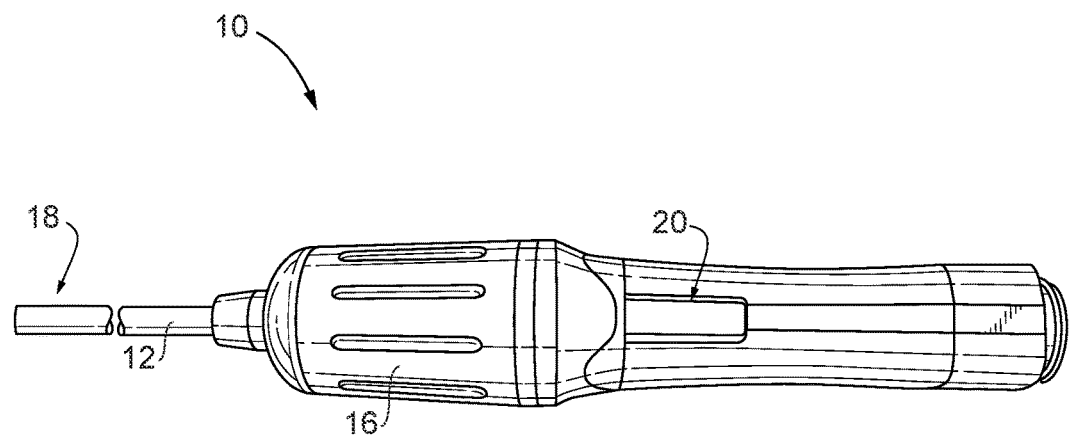
FIG. 1 shows a handle portion of the deflectable vascular catheter with a deflection indication drive screw in a first position that corresponds to the distal end portion of the catheter shaft being aligned with a longitudinal axis of the catheter shaft.

Referring now to the drawings wherein like reference numerals identify similar structural elements and features of the subject invention, there is illustrated in FIGS. 1 through 4 a new and useful deflectable vascular catheter that includes a proximal handle assembly 10, an elongated catheter shaft 12 extending distally from the proximal handle assembly 10 and including a deflectable distal end portion 18 (shown in FIG. 4), and a linear drive screw 14, that is operatively associated with an interior cavity of the proximal handle assembly 10 for deflecting the distal end portion 18 of the catheter shaft 12.

Figure 4:
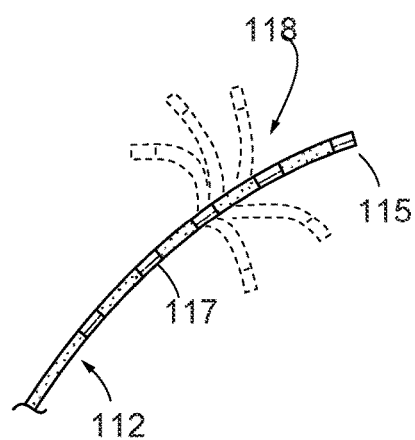
FIG. 4 shows a perspective view of a distal end portion of a bidirectional ablation catheter, configured to use the drive screw of FIG. 1, illustrating an exemplary range of curved deflection.
Figure 5:
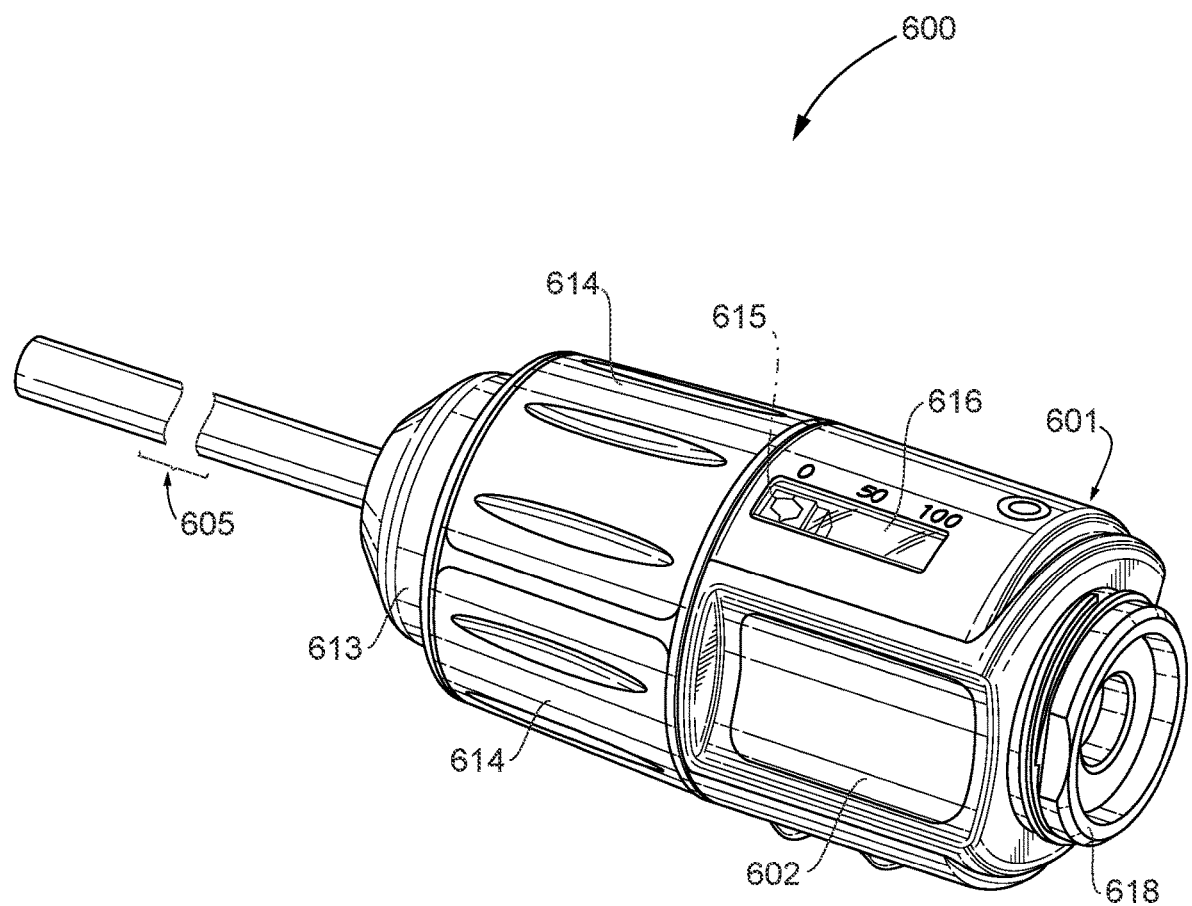
FIG. 5 shows a perspective view of the deflectable vascular catheter of FIG. 1 including a proximal handle assembly showing another embodiment of the deflection indication feature of the subject invention.

More particularly, the linear drive screw 14 is adapted and configured to steer or otherwise move the distal end portion 18 of the catheter shaft 12 between a first position where the distal end portion of the catheter shaft 12 is axially aligned with a longitudinal axis of the catheter shaft and a second position where the distal end portion of the catheter shaft is deflected angularly away from the longitudinal axis of the catheter shaft 12, as shown for example in FIG. 4. It is envisioned that the distal end portion 18 of the catheter shaft 12 could be configured with a maximum curved deflection angle that ranges from 90 degrees to 270 degrees. It is further envisioned that the distal end portion 18 of the catheter shaft 12 could have a distance between 50 mm and 7 mm from the proximal portion of the shaft 12 when fully deflected. The catheter shaft 12 can also gradually narrow towards the distal direction and have a diameter ranging from 3 F to 13 F, and preferably from 5 F to 12 F.

In accordance with a preferred embodiment of the subject invention, the catheter also includes a position indicator associated with the drive screw 14 for providing a visual indication of the position of the drive screw 14, which corresponds to a degree of curved deflection of the deflectable distal end portion 18 of the catheter shaft 12. It is envisioned that the indicator means can comprise a contrasting color as shown for example in FIGS. 2 and 3, or it could be indicia such as symbols or numbering, or even a structural feature that is provided on at least a portion of the linear drive screw 14.

In addition, a window or portal 20 is formed in the proximal handle assembly 12 at a location that is aligned with the drive screw 14 for viewing at least the portion of the drive screw 14 that includes the indicator means as the drive screw 14 moves within the interior cavity of the proximal handle assembly 10 to steer the distal end portion 18 of the catheter shaft 12. The drive screw 14 provides a critical visual guide for the surgeon to determine the amount or degree of deflection of the distal end portion 18 of the catheter shaft 12 when navigating within the vasculature of a patient, without having to perform visual observation under X-ray of a radiopaque marker band located on the distal-most tip of the catheter. The drive screw 14 not only provides an indicator of whether the tip is neutral or deflected, but shows the extent to which the distal end portion 18 is deflected. An example of a bidirectional drive screw mechanism is described in detail in commonly assigned U.S. Pat. No. 9,572,957, the disclosure of which is herein incorporated by reference in its entirety. It is noted that the drive screw 14 is capable of showing the progression of bending and straightening in a first direction and bending in a second direction as shown in FIG. 4.

The deflectable vascular catheter of the subject invention further includes a rotatable control knob 16 that is operatively associated with a distal end portion of the proximal handle assembly 10 for moving or otherwise actuating the drive screw 14. The window 20 is located adjacent or proximal to the rotatable control knob 16.

In use, when the control knob 16 is manually rotated by a surgeon, the colored drive shaft 14 will translate linearly within the interior cavity of the proximal handle portion 10, causing steering wires within the catheter shaft 12 to steer the deflectable distal end portion 18 of the catheter shaft 12.

At such a time, the linear movement of the colored drive screw 14 is readily observable through the window 20 in the proximal handle portion 10, which will correspond to the amount of deflection of the distal end portion 18 of the catheter shaft 12.

Figure 2:
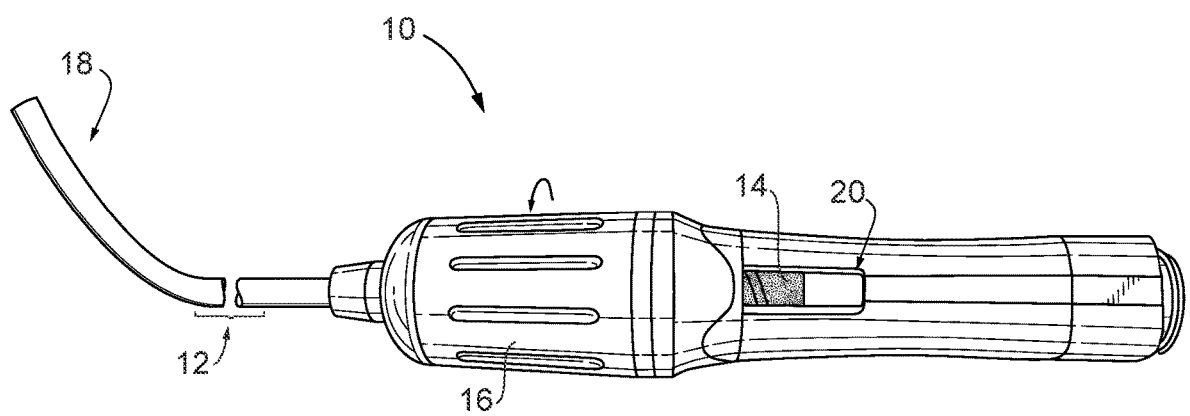
FIG. 2 shows the drive screw of the deflectable vascular catheter of FIG. 1 in a second position that corresponds to the catheter shaft being partially deflected relative to the longitudinal axis of the catheter shaft.

More particularly, when the deflectable distal end portion 18 of a catheter shaft 12 is aligned with a longitudinal axis of the catheter shaft 12, the colored drive screw 14 (or at least a colored portion thereof) is not visible through or otherwise within the window 20, as shown in FIG. 1. Then, when the deflectable distal end portion 18 of the catheter shaft 12 is deflected into a partially curved orientation (see FIG. 4 for example), the colored drive screw 14 (or at least a colored portion thereof) is partially visible through or otherwise within the window 20, as shown in FIG. 2.

Figure 3:
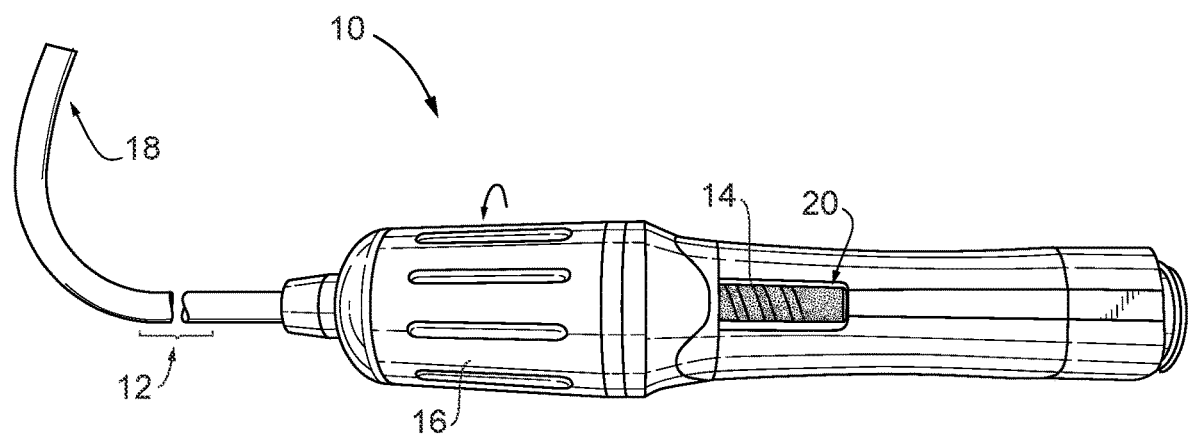
FIG. 3 shows the drive screw of the deflectable vascular catheter of FIG. 1 with the deflection indication feature of the subject invention in a third position that corresponds to the catheter shaft being deflected to a maximum curvature relative to the longitudinal axis of the catheter shaft.

Finally, when the deflectable distal end portion 18 of the catheter shaft 12 is deflected into a maximum curved orientation, the colored drive screw 14 (or at least a colored portion thereof) is completely visible through or otherwise within the window 20, as shown in FIG. 3. In other words, the window 20 is completely filled with contrasting color (relative to the color of the handle portion itself), indicating that the deflectable distal end portion 18 of catheter shaft 12 has reached its maximum degree of curvature, without the need for X-ray observation techniques. Alternatively, the device could be configured so that a filled window indicates that the distal end portion of the catheter shaft is axially aligned, and an empty widow indicates that the distal end portion of the catheter shaft is at maximum deflection.

To the extent that X-ray observation is still necessary during an intravascular procedure, for example, to ensure a proper positioning of the catheter tip within the vasculature of a patient, a marker ring 115 is located at the distal-most end of the catheter shaft 112, as shown in FIG. 4. It is envisioned that the catheter shaft 12 could be configured as a guiding sheath as shown in FIGS. 1-3, or as an ablation catheter as shown in FIG. 4, which would include a plurality of spaced apart electrode rings 117 spaced along the length of the distal end portion 118 of the catheter shaft 112. Alternatively, the catheter shaft could be configured as an irrigation catheter, a drainage catheter or the like.

It is also envisioned that the deflection indication feature of the subject invention could be employed with bi-directional deflectable vascular catheters as shown in FIG. 4, for example and described in detail in commonly assigned U.S. Pat. No. 9,498,602, the disclosure of which is herein incorporated by reference in its entirety. In such a device, there may be two separate linear drive screws, and therefore more than one window could be provided in the handle portion, and/or more than one contrasting color could be used in connection with the multiple drive screws to provide a visual indication to an observer relative to each direction of curvature.

Referring now to the FIGS. 5-10 wherein like reference numerals identify similar structural elements and features of the subject there is illustrated a new and useful deflectable vascular catheter device 600 constructed in accordance with the subject invention. The deflectable vascular catheter 600 includes an elongated sheath 605 extending distally from the proximal handle assembly 601 and including a deflectable distal end portion, similar to that shown in FIGS. 1-4. Deflectable vascular catheter 600 includes deflection knob 603 which when turned manually by the surgeon, causes steering wires 620 within the elongated sheath 605 to steer the distal end portion of the elongated sheath 605. It is envisioned that the distal end portion of the elongated sheath 605 could be configured with a maximum curved deflection angle that ranges from 90 degrees to 270 degrees.

Figure 10:
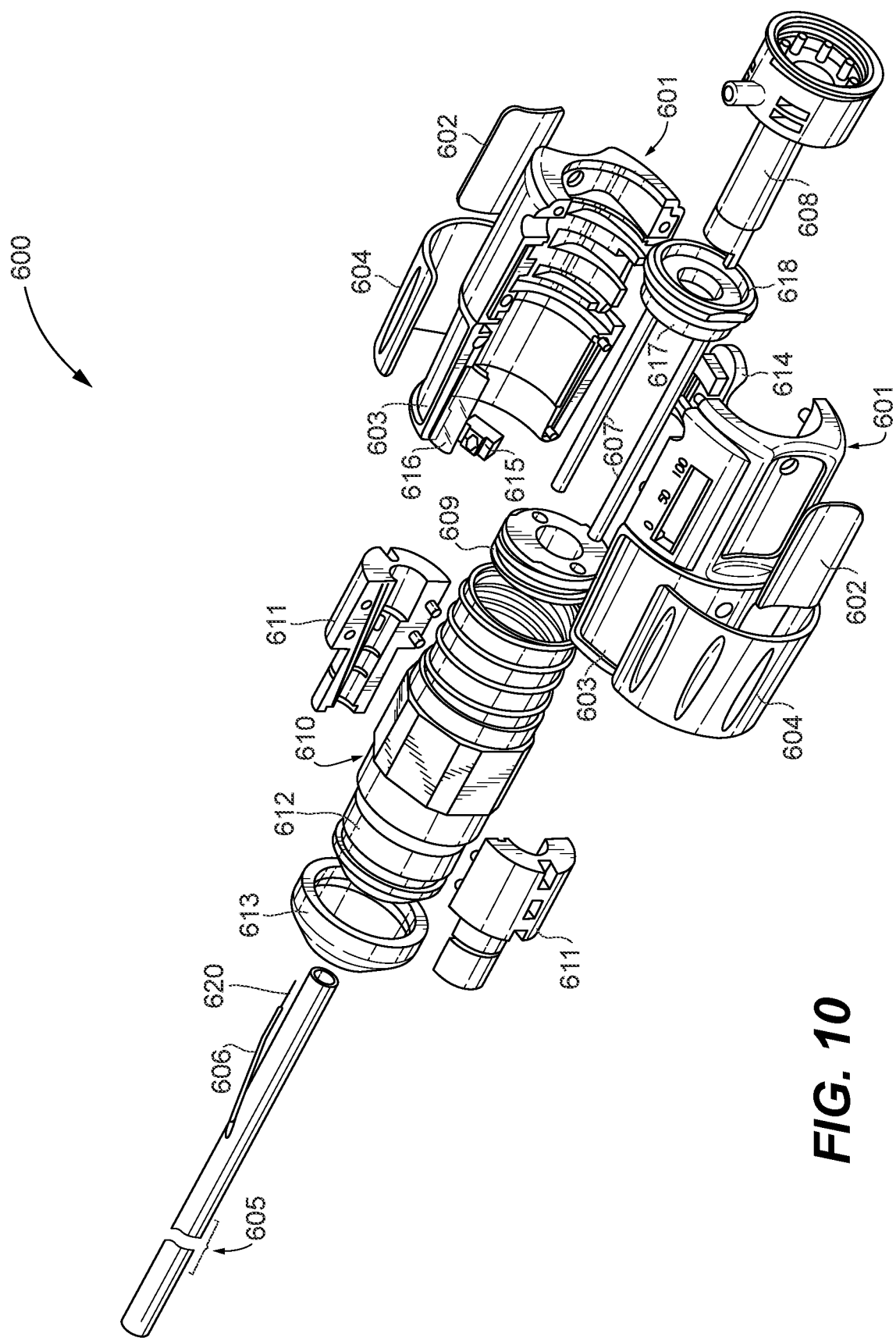
FIG. 10 provides an exploded view of the deflectable vascular catheter shown in FIG. 5, with parts separated for ease of illustration including the deflection indicator.

In accordance with a preferred embodiment of the subject invention, the catheter includes an indicator 615 which shows the user the approximate amount or degree of deflection that the distal end portion has curved through a window 616 with associated markings (e.g., 0, 50, 100), as shown in FIG. 10, allowing the surgeon to reach a specific curve when navigating within the vasculature of a patient, without the use of X-ray observation techniques or external screens. It is further considered that the deflectable vascular catheter device 600 can include a brake lock 614. Once a desired deflection angle is reached brake lock 614 is slid into place to lock the drive gear 609 from further moving along guide rods 607 and further actuating the steering wires 620, in order to allow the surgeon to perform the next steps of the procedure without worrying that the deflection knob 603 will turn. The moving deflection indictor 615 is actuated when the deflection knob 603 is twisted by the surgeon. As the deflection knob 603 is twisted, the drive gear 609 is moved along the guide rods 607, and directs the deflection indicator to move within the window 616.

Figure 6:
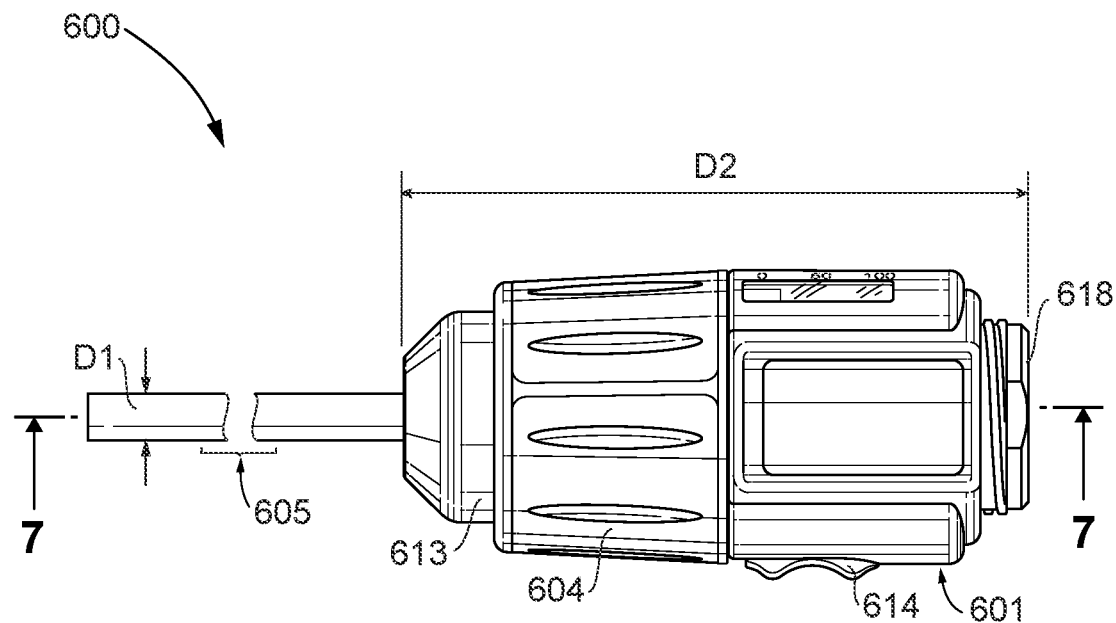
FIG. 6 provides a front side view of the deflectable vascular catheter shown in FIG. 5.
Figure 7:
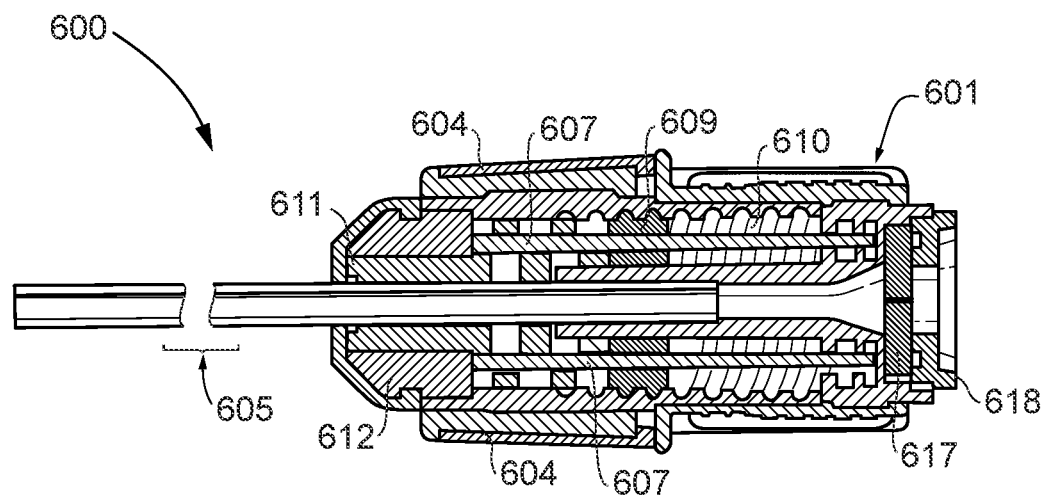
FIG. 7 provides a sectional view of the deflectable vascular catheter shown in FIG. 6, showing the inside of the handle assembly.
Figure 8:
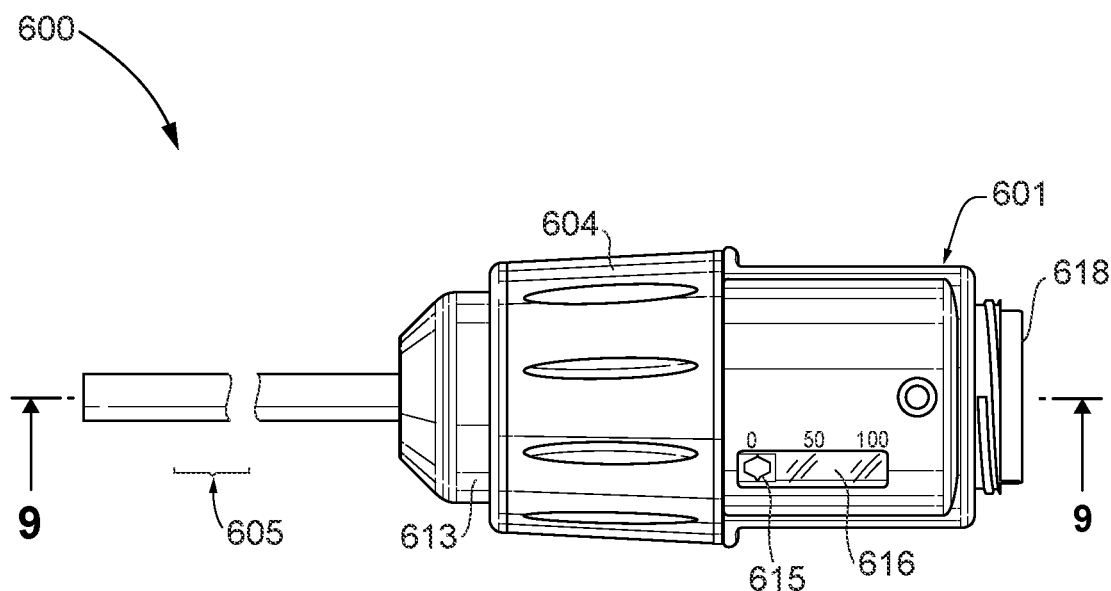
FIG. 8 provides top plan view of the deflectable vascular catheter shown in FIG. 5.
Figure 9:
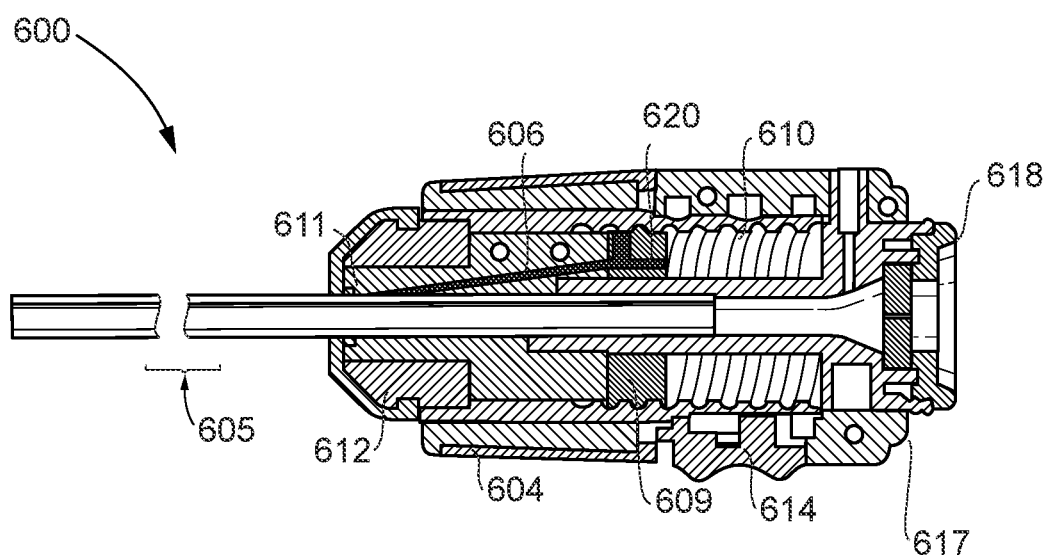
FIG. 9 provides a sectional view of the deflectable vascular catheter shown in FIG. 8, showing the inside of the handle assembly at a second elevation.

The handle assembly, which includes a handle 601 with finger grips 602, for the device shown in FIGS. 6 through 11 is relatively small, as compared to the handles of prior art devices of this type, in that it is preferably not longer than 5 cm as compared to 15 cm or longer for handles of devices that are currently in the marketplace, depicted as D2 in FIG. 6. This is made possible by the compact design of the guide rods 607 and drive gear 609 sitting within threaded sleeve 610. A sheath hub 608 sits between the guide rods 607 and is inserted through the drive gear 609 and into the threaded sleeve 610, and engages the sheath 605 and steering wires 620. The deflectable vascular catheter 600 can use a deflectable guiding sheath 605 having a diameter range of 3 F to 13 F, and preferably from 5 F to 12 F, shown as D1 in FIG. 6.

Threaded sleeve 610 is surrounded by a pair of sheath supports 611 situated opposite each other. A sheath support sleeve 612 is fitted on the outside of the distal ends of the sheath supports 611. The sheath can be supported at a distal end of the sheath support sleeve 612 by a strain relief cap 613. The strain relief cap 613 can be fixed to the sheath support sleeve 612 in any suitable manner (e.g., adhesive).

Referring further to FIGS. 6 and 10, window 616 covering the deflection indicator 615 is held in place by deflection knob 603. Deflection knob 603 is covered by an overmold grip 604 to prevent a surgeon's hand from slipping when using the deflectable vascular catheter device 600. A hemostatic seal 617 and a seal retainer 618 are used on a proximate end of the deflectable vascular catheter device 600 to minimize blood loss and embolisms during a procedure.

Referring further to FIGS. 6 and 10, window 616, covering, the deflection indicator 615, is held in place by deflection knob 603. Deflection knob 603 is covered by an overmold grip 604 to prevent a surgeon's hand from slipping when using the deflectable vascular catheter device 600. A hemostatic seal 617 and a seal retainer 618 are used on a proximate end of the deflectable vascular catheter device 600 to minimize blood loss and embolisms during a procedure.

While the deflectable vascular catheter of the subject disclosure has been shown and described with reference to preferred embodiments, those skilled in the art will readily appreciate that changes and/or modifications may be made thereto without departing from the scope of the subject disclosure.

What is claimed is:

1. A deflectable vascular catheter, comprising:
   a) an elongated sheath comprising a sheath lumen extending along a longitudinal axis from a proximal sheath portion to a deflectable distal sheath portion;
   b) a proximal handle assembly comprising:
      i) catheter support having a sidewall defining a catheter support lumen, wherein the proximal portion of the elongated sheath resides in the catheter support lumen;
      ii) a catheter support sleeve contacting the sidewall of the catheter support so that the catheter support resides inside the catheter support sleeve;
      iii) an internally threaded sleeve extending from a proximal open end to a distal open end, wherein a proximal portion of the internally threaded sleeve has internal threads that extend distally from the proximal open end to a distal portion of the threaded sleeve that is devoid of internal threads but surrounds a proximal portion of the catheter support sleeve in turn supporting the catheter support supporting the proximal portion of the elongated sheath;
      iv) a drive gear housed inside and threadingly engaged with the internal threads of the threaded sleeve, wherein the drive gear comprises a drive gear central opening positioned between opposed drive gear first and second secondary openings;
      v) at least one steering wire extending distally v) from the drive gear to the distal end portion of the elongated sheath;
      vi) a proximal sheath hub abutting the internally threaded sleeve at the proximal open end thereof, wherein the proximal sheath hub comprises a distally extending sheath hub sleeve having a sheath hub lumen, the sheath hub sleeve extending distally through the central opening in the drive gear, and wherein the proximal portion of the elongated sheath is received in the sheath hub sleeve so that the sheath hub lumen is in open communication with the sheath lumen;
      vii) a proximal seal retainer supporting first and second guide rods, wherein the first guide rod extends to first guide rod proximal and distal ends and the second guide rod extends to second guide rod proximal and distal ends, and wherein the first and second guide rods extend distally from the proximal seal retainer and through the opposed first and second secondary openings in the drive gear in a parallel side-by-side relationship with their respective distal ends being connected to the sheath support housed inside the sheath sleeve; and
      viii) a deflection knob connected to an outer surface of the internally threaded sleeve,
   c) wherein manipulation about the longitudinal axis of the deflection knob connected to the internally threaded sleeve threadingly engaged with the drive gear selectively moves the drive gear in a distal or a proximal axial direction along the sheath hub sleeve extending through the drive gear central opening and along the side-by-side first and second guide rods extending through the opposed first and second secondary openings in the drive gear to thereby selectively actuate the at least one steering wire to deflect the distal end portion of the elongated sheath between a first position aligned with the longitudinal axis of the elongated sheath and a second position deflected angularly away from the longitudinal axis.

2. The deflectable vascular catheter of claim 1, wherein an indicator means is associated with the drive gear, the indicator means providing a visual indication of the position of the drive gear, which corresponds to a degree of curved or angular deflection of the deflectable distal portion of the elongated sheath.

3. The deflectable vascular catheter of claim 2, wherein the indicator means includes indicia, coloring or structure provided on or operatively associated with at least a portion of the drive gear.

4. The deflectable vascular catheter of claim 2, wherein a window in the proximal handle assembly is configured for viewing the indicator means as the drive gear moves axially in the distal or proximal directions along the sheath hub sleeve extending through the drive gear central opening and along the side-by-side first and second guide rods extending through the opposed first and second secondary openings in the drive gear to deflect the distal portion of the elongated sheath with respect to the longitudinal axis.

5. The deflectable vascular catheter of claim 1, wherein the elongated sheath gradually narrows towards its deflectable distal sheath portion.

6. The deflectable vascular catheter of claim 4, wherein the window in the proximal handle assembly is located adjacent to the rotatable control knob.

7. The deflectable vascular catheter of claim 1, wherein the elongated sheath is configured as a guiding sheath.

8. The deflectable vascular catheter of claim 1, wherein the elongated sheath is configured as an ablation catheter.

9. The deflectable vascular catheter of claim 1, wherein the distal portion of the elongated sheath is configured for a curved deflection angle that ranges from 90 degrees to 270 degrees with respect to the longitudinal axis.

10. The deflectable vascular catheter of claim 1, wherein the elongated sheath has a diameter of 3 F to 13 F.

11. A deflectable vascular catheter, comprising:
   a) an elongated sheath comprising a sheath lumen extending along a longitudinal axis from a proximal sheath portion to a deflectable distal sheath portion;
   b) a proximal handle assembly comprising:
      i) catheter support having a sidewall defining a catheter support lumen, wherein the proximal portion of the elongated sheath resides in the catheter support lumen;
      ii) a catheter support sleeve contacting the sidewall of the catheter support so that the catheter support resides inside the catheter support sleeve;
      iii) an internally threaded sleeve extending from a proximal open end to a distal open end, wherein a proximal portion of the internally threaded sleeve has internal threads that extend distally from the proximal open end to a distal portion of the threaded sleeve that is devoid of internal threads but surrounds a proximal portion of the catheter support sleeve in turn supporting the catheter support supporting the proximal portion of the elongated sheath;
      iv) a drive gear housed inside and threadingly engaged with the internal threads of the threaded sleeve, wherein the drive gear comprises a drive gear central opening positioned between opposed drive gear first and second secondary openings;
      v) at least one steering wire extending distally from the drive gear to the distal end portion of the elongated sheath;
      vi) a proximal sheath hub abutting the internally threaded sleeve at the proximal open end thereof, wherein the proximal sheath hub comprises a distally extending sheath hub sleeve having a sheath hub lumen, the sheath hub sleeve extending distally through the central opening in the drive gear, and wherein the proximal portion of the elongated sheath is received in the sheath hub sleeve so that the sheath hub lumen is in open communication with the sheath lumen;

vii) a proximal seal retainer supporting first and second guide rods, wherein the first guide rod extends to first guide rod proximal and distal ends and the second guide rod extends to second guide rod proximal and distal ends, and wherein the first and second guide rods extend distally from the proximal seal retainer and through the opposed first and second secondary openings in the drive gear in a parallel side-by-side relationship with their respective distal ends being connected to the sheath support housed inside the sheath sleeve;

viii) a deflection knob connected to an outer surface of the internally threaded sleeve;

ix) an indicator means associated with the drive gear; and x) a window in the proximal handle assembly, wherein the window is configured for viewing the indicator means, c) wherein manipulation about the longitudinal axis of the deflection knob connected to the internally threaded sleeve threadingly engaged with the drive gear selectively moves the drive gear and the associated indicator means in a distal or a proximal axial direction along the sheath hub sleeve extending through the drive gear central opening and along the side-by-side first and second guide rods extending through the opposed first and second secondary openings in the drive gear to thereby selectively actuate the at least one steering wire to deflect the distal end portion of the elongated sheath between a first position aligned with the longitudinal axis of the elongated sheath and a second position deflected angularly away from the longitudinal axis, and d) wherein the indicator means associated with the drive gear provides a visual indication through the window in the proximal handle assembly of the position of the drive gear, which corresponds to a degree of curved or angular deflection of the deflectable distal portion of the elongated sheath.

12. The deflectable vascular catheter of claim 11, wherein the indicator means includes indicia, coloring or structure provided on or operatively associated with at least a portion of the drive gear.

13. The deflectable vascular catheter of claim 11, wherein the window in the proximal handle assembly is located adjacent to the rotatable control knob.

14. The deflectable vascular catheter of claim 11, wherein the elongated sheath is configured as a guiding sheath.

15. The deflectable vascular catheter of claim 11, wherein the elongated sheath is configured as an ablation catheter.

16. The deflectable vascular catheter of claim 11, wherein the distal portion of the elongated sheath is configured for a curved deflection angle that ranges from 90 degrees to 270 degrees with respect to the longitudinal axis.

17. The deflectable vascular catheter of claim 11, wherein the elongated sheath has a diameter of 3 F to 13 F.

18. The deflectable vascular catheter of claim 11, wherein the elongated sheath gradually narrows towards its deflectable distal sheath portion.

19. A deflectable vascular catheter, comprising:
a) an elongated sheath comprising a sheath lumen extending along a longitudinal axis from a proximal sheath portion to a deflectable distal sheath portion;
b) a proximal handle assembly comprising:
   i) catheter support having a sidewall defining a catheter support lumen, wherein the proximal portion of the elongated sheath resides in the catheter support lumen;
   ii) a catheter support sleeve contacting the sidewall of the catheter support so that the catheter support resides inside the catheter support sleeve;
   iii) an internally threaded sleeve extending from a proximal open end to a distal open end, wherein a proximal portion of the internally threaded sleeve has internal threads that extend distally from the proximal open end to a distal portion of the threaded sleeve that is devoid of internal threads but surrounds a proximal portion of the catheter support sleeve in turn supporting the catheter support supporting the proximal portion of the elongated sheath;
   iv) a colored drive gear housed inside and threadingly engaged with the internal threads of the threaded sleeve, wherein the colored drive gear comprises a drive gear central opening positioned between opposed drive gear first and second secondary openings;
   v) at least one steering wire extending distally from the colored drive gear to the distal end portion of the elongated sheath;
   vi) a proximal sheath hub abutting the internally threaded sleeve at the proximal open end thereof, wherein the proximal sheath hub comprises a distally extending sheath hub sleeve having a sheath hub lumen, the sheath hub sleeve extending distally through the central opening in the colored drive gear, and wherein the proximal portion of the elongated sheath is received in the sheath hub sleeve so that the sheath hub lumen is in open communication with the sheath lumen;
   vii) a proximal seal retainer supporting first and second guide rods, wherein the first guide rod extends to first guide rod proximal and distal ends and the second guide rod extends to second guide rod proximal and distal ends, and wherein the first and second guide rods extend distally from the proximal seal retainer and through the opposed first and second secondary openings in the colored drive gear in a parallel side-by-side relationship with their respective distal ends being connected to the sheath support housed inside the sheath sleeve;
   viii) a deflection knob connected to an outer surface of the internally threaded sleeve; and
   ix) a window in the proximal handle assembly, wherein the window is configured for viewing the indicator means,
c) wherein manipulation about the longitudinal axis of the deflection knob connected to the internally threaded sleeve threadingly engaged with the colored drive gear selectively moves the drive gear in a distal or a proximal axial direction along the sheath hub sleeve extending through the drive gear central opening and along the side-by-side first and second guide rods extending through the opposed first and second secondary openings in the colored drive gear to thereby selectively actuate the at least one steering wire to deflect the distal end portion of the elongated sheath between a first position aligned with the longitudinal axis of the elongated sheath and a second position deflected angularly away from the longitudinal axis, and d) wherein, when the deflectable distal end portion of catheter shaft is in the first position aligned with the longitudinal axis of the catheter shaft, the colored drive screw is either visible or not visible through the window, and wherein, when the deflectable distal end portion of the elongated sheath is deflected into the second position angularly away from the longitudinal axis, the colored drive gear is the other of not visible or visible through the window in the proximal handle assembly to an extent that corresponds to a degree of curved or angular deflection of the deflectable distal portion of the elongated sheath.

20. The deflectable vascular catheter of claim 19, wherein when the deflectable distal end portion of the elongated sheath is deflected into a maximum curved orientation, the colored drive gear is completely visible through the window in the proximal handle assembly or, wherein when the deflectable distal end portion of the elongated sheath is deflected into a maximum curved orientation, the colored drive gear is not visible through the window in the proximal handle assembly.

\* \* \* \* \*